(12) United States Patent
Komiya et al.

(10) Patent No.: US 10,048,184 B2
(45) Date of Patent: Aug. 14, 2018

(54) CRACK SENSOR AND CRACK MONITORING DEVICE

(71) Applicant: TOSHIBA TEC KABUSHIKI KAISHA, Shinagawa-ku, Tokyo (JP)

(72) Inventors: Kenichi Komiya, Kanagawa (JP); Daisuke Ishikawa, Shizuoka (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/989,853

(22) Filed: Jan. 7, 2016

(65) Prior Publication Data

US 2016/0202161 A1  Jul. 14, 2016

(30) Foreign Application Priority Data

Jan. 14, 2015 (JP) ................. 2015-004957

(51) Int. Cl.
| | |
|---|---|
| *G01N 19/08* | (2006.01) |
| *G01N 3/40* | (2006.01) |
| *G01N 29/24* | (2006.01) |
| *G01N 27/20* | (2006.01) |
| *G01N 27/24* | (2006.01) |

(Continued)

(52) U.S. Cl.
CPC .............. *G01N 3/40* (2013.01); *G01N 27/20* (2013.01); *G01M 5/0033* (2013.01); *G01N 19/08* (2013.01); *G01N 27/205* (2013.01); *G01N 27/24* (2013.01); *G01N 29/2475* (2013.01); *G01N 33/383* (2013.01); *G01N 2203/0062* (2013.01);
(Continued)

(58) Field of Classification Search
CPC .......... G01N 19/08; G01N 2203/0062; G01N 2291/0258; G01N 2291/106; G01N 27/20; G01N 27/205; G01N 27/24; G01N 29/2475; G01N 3/40; G01N 33/383; G01M 5/0033
USPC .............................. 73/776.799; 324/557, 691
See application file for complete search history.

(56) References Cited

U.S. PATENT DOCUMENTS

| | | | | |
|---|---|---|---|---|
| 4,255,974 A | * | 3/1981 | Dufrane | G01B 7/18 73/776 |
| 4,484,132 A | * | 11/1984 | Crites | G01N 27/205 324/557 |

(Continued)

FOREIGN PATENT DOCUMENTS

| | | |
|---|---|---|
| JP | 11-211644 | 8/1999 |
| JP | 2014-032057 | 2/2014 |
| JP | 2014032057 A  * | 2/2014 |

OTHER PUBLICATIONS

Japanese Office Action for Japanese Patent Application No. 2015-004957 dated Apr. 25, 2017.

*Primary Examiner* — Jonathan Dunlap
(74) *Attorney, Agent, or Firm* — Amin, Turocy & Watson LLP (57) ABSTRACT

A crack sensor for detecting the extension of a crack comprises an insulator base material made from an insulating material, a common line formed on the insulator base material along a first direction and a plurality of gauge lead wires which is formed on the insulator base material and each of which has an end connected with the common line at an interval and another end extending in a second direction orthogonal to the first direction, wherein the extending end reaches a position to which the extending end retreats in a direction opposite to the first direction with respect to the end connected with the common line.

6 Claims, 4 Drawing Sheets (51) Int. Cl.
*G01M 5/00* (2006.01)
*G01N 33/38* (2006.01)

(52) U.S. Cl.
CPC ............... *G01N 2291/0258* (2013.01); *G01N 2291/106* (2013.01)

(56) References Cited

U.S. PATENT DOCUMENTS

| | | | | |
|---|---|---|---|---|
| 5,142,141 A * | 8/1992 | Talat | ................... | G01M 11/086 250/227.15 |
| 5,201,229 A * | 4/1993 | Ibe | ...................... | G01N 27/205 73/776 |
| 5,440,300 A * | 8/1995 | Spillman, Jr. | ....... | B60C 23/0444 250/227.21 |
| 6,717,420 B2 * | 4/2004 | Eyraud | ................ | F01D 11/122 324/701 |
| 6,973,838 B2 * | 12/2005 | Denis | .................. | G01M 5/0033 73/799 |
| 7,231,832 B2 * | 6/2007 | Woodard | ................ | G01N 3/38 73/779 |
| 7,387,033 B2 * | 6/2008 | Qing | .................. | G01D 5/35383 73/587 |
| 7,473,077 B2 * | 1/2009 | Gaffiero | ................ | B64C 27/007 416/230 |
| 7,950,289 B2 * | 5/2011 | Foote | ................... | G01M 5/0033 73/760 |
| 8,059,008 B2 * | 11/2011 | Marincak | ............... | G01N 27/24 324/691 |
| 8,151,623 B2 * | 4/2012 | Shinde | .................... | F01D 17/02 73/7 |
| 8,886,388 B2 * | 11/2014 | Moser | ................ | G01M 5/0033 701/29.1 |
| 2005/0223812 A1 * | 10/2005 | Denis | .................. | G01M 5/0033 73/799 |
| 2006/0079747 A1 * | 4/2006 | Beard | ................ | G01N 29/043 600/407 |
| 2006/0132149 A1 * | 6/2006 | Twerdochlib | ............ | G01B 7/18 324/693 |
| 2006/0154398 A1 * | 7/2006 | Qing | ...................... | G01M 5/00 438/48 |
| 2013/0298646 A1 * | 11/2013 | Ohl | ........................ | G01N 13/00 73/60.11 |
| 2015/0114122 A1 * | 4/2015 | Soles | .................. | G08B 13/126 73/584 |

* cited by examiner

CRACK SENSOR AND CRACK MONITORING DEVICE

CROSS-REFERENCE TO RELATED APPLICATION

This application is based upon and claims the benefit of priority from Japanese Patent Application No. P2015-004957, filed Jan. 14, 2015, the entire contents of which are incorporated herein by reference.

FIELD

Embodiments described herein relate generally to a crack sensor and a crack monitoring device for detecting a crack (fissure, crackle) on a construction such as a bridge, a tunnel and the like.

BACKGROUND

A crack sensor is proposed that detects a crack (fissure, crackle) generated in a construction such as a bridge, a tunnel and the like, for example, a two-dimensionally extending crack which extends horizontally after extending vertically (see Japanese Unexamined Patent Application Publication No. Hei 11-211644).

In the two-dimensional crack sensor, a first planar resistor is arranged on the surface of an insulator base adhered on the wall surface of an inspected object. An intermediate insulator is arranged on the surface of the first planar resistor. A second planar resistor is arranged on the surface of the insulator. The first and the second planar resistors are separately formed into a structure consisting of a plurality of parallel resistance wires which is deployed at intervals. Moreover, the resistance wires of the first planar resistor are orthogonal to those of the second planar resistor.

The first and the second planar resistors are connected with the lead wire connecting sections arranged at two ends of each resistance wire. For example, the resistance value of the first planar resistor changes when a resistance wire of the first planar resistor is cut off. The extension of a crack is determined by measuring the current between the lead wire connecting sections located at two ends of each resistance wire.

In the two-dimensional crack sensor disclosed in Japanese Unexamined Patent Application Publication No. Hei 11-211644, through a laminated structure in which the intermediate insulator is sandwiched between the first planar resistor and the second planar resistor, the outmost insulator base is adhered on the surface of a measured object such as concrete.

As the crack generated on the concrete extends, the insulator base is broken with the extension of the crack. Consequentially, the resistance wires of the first planar resistor are broken.

However, as the intermediate insulator is sandwiched between the second planar resistor and the insulator base, it is hard for the breaking force resulting from the breaking of the insulator base to spread to the resistance wires of the second planar resistor, and the resistance wires of the second planar resistor may not be broken. In this case, the effect of the two-dimensional sensor cannot be exerted fully.

DETAILED DESCRIPTION

The problem the present invention intends to solve is to provide a crack sensor for detecting the extension of a crack.

The crack sensor comprises an insulator base material made from an insulating material, a common line formed on the insulator base material along a first direction and a plurality of gauge lead wires which is formed on the insulator base material and each of which has an end connected with the common line at interval and another end extending in a second direction orthogonal to the first direction, wherein the extending end reaches a position to which the extending end retreats in a direction opposite to the first direction with respect to the end connected with the common line.

Embodiments of the present invention are described below with reference to the accompanying drawings.

First Embodiment

Figure 1:
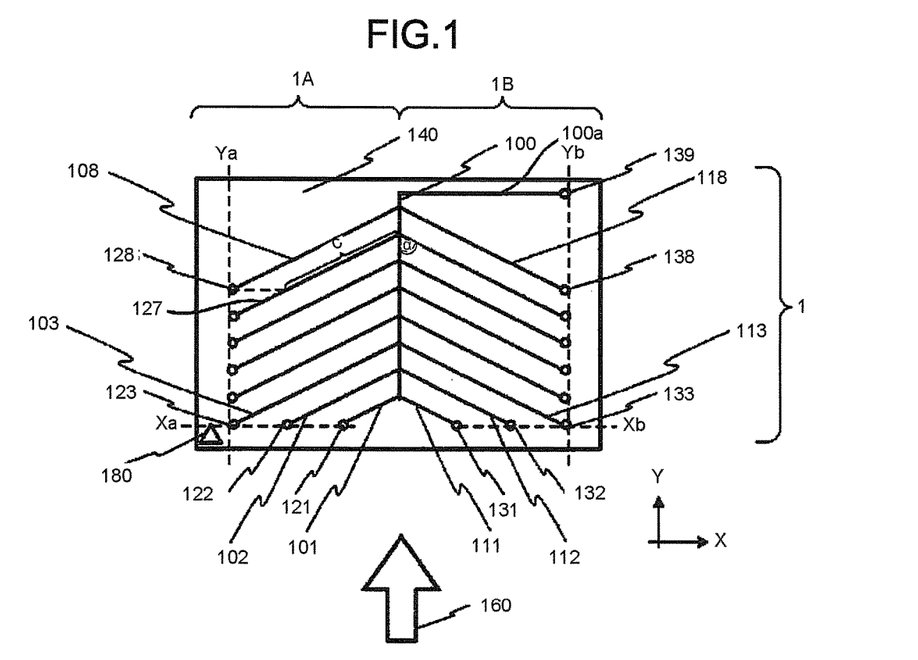
FIG. 1 is a top view of a crack sensor according to a first embodiment.
Figure 2:
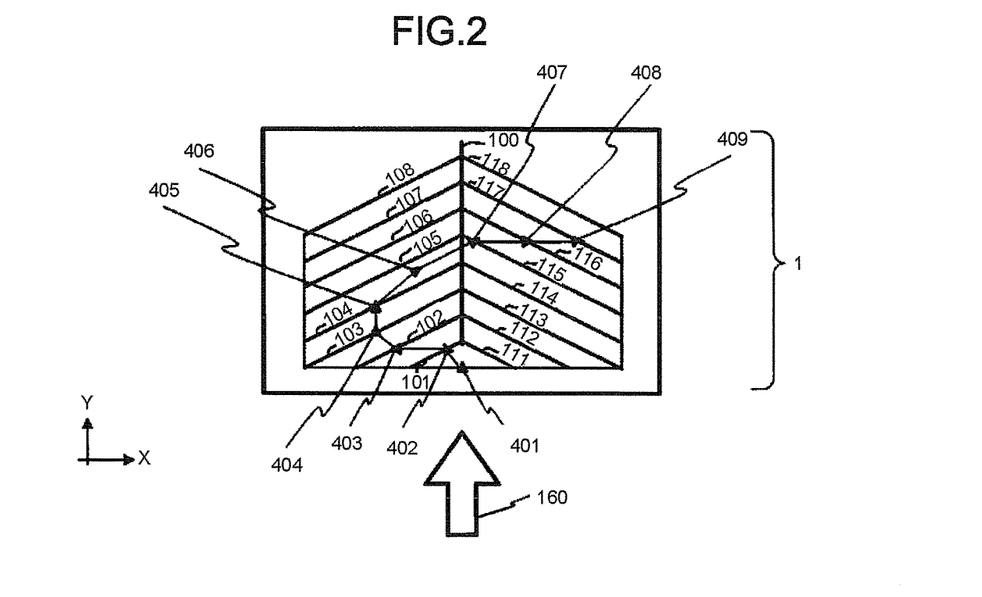
FIG. 2 is a diagram illustrating the relationship between the crack sensor shown in FIG. 1 and the extension direction of a crack generated in a monitored object.
Figure 3:
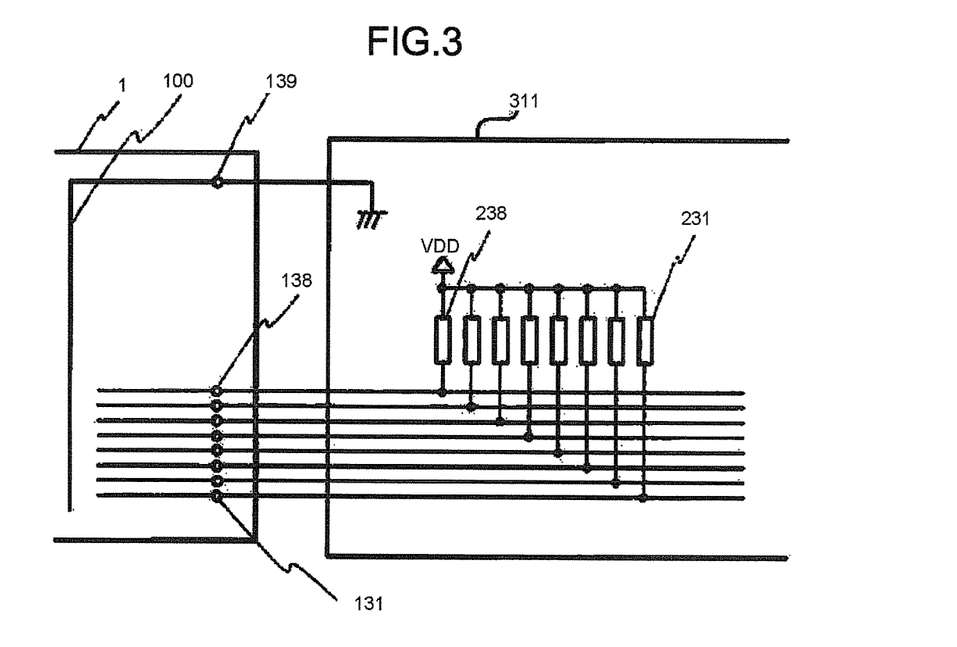
FIG. 3 is a diagram illustrating a circuit structure (an interface section) for acquiring a detection signal of the crack sensor shown in FIG. 1 as digital data.
Figure 4:
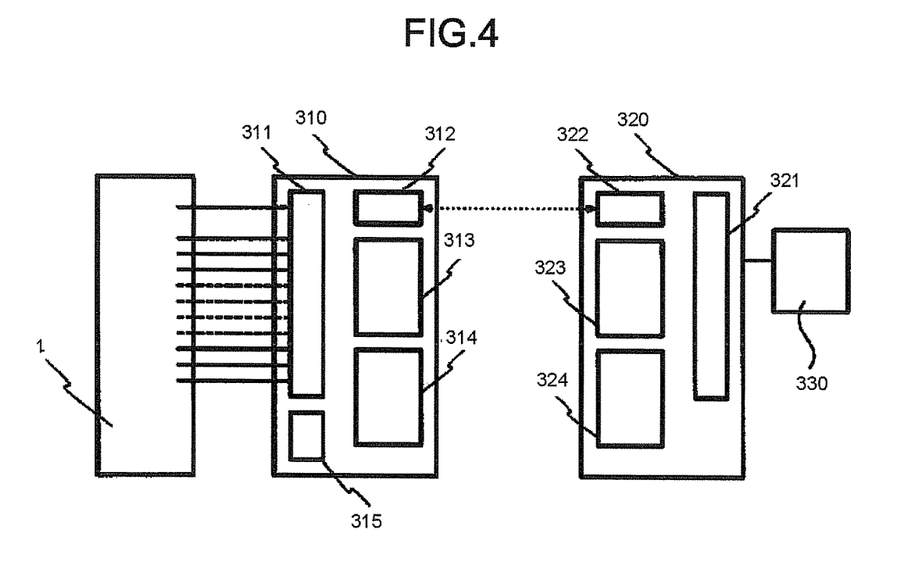
FIG. 4 is a block diagram illustrating the circuit structure of a crack monitoring device for monitoring a crack according to the information output from the interface section shown in FIG. 3.

FIG. 1 is a top view of a crack sensor according to a first embodiment. FIG. 2 is a diagram illustrating the relationship between the crack sensor shown in FIG. 1 and the extension direction of a crack generated in a monitored object. FIG. 3 is a diagram illustrating a circuit structure (an interface section) for acquiring a detection signal of the crack sensor shown in FIG. 1 as digital data. FIG. 4 is a block diagram illustrating the circuit structure of a crack monitoring device for monitoring a crack according to the information output from the interface section shown in FIG. 3.

The crack sensor 1 comprises, on a quadrangular base material 140 made from a film-shaped insulating material (e.g. polyester resin or polyimide resin), a common line 100 formed by a wiring pattern conductor (an alloy of copper and nickel, aluminum, silver, etc.); a terminal 139 for connecting the common line 100 with the outside of the crack sensor; a plurality of gauge lead wires (the alloy of copper and nickel, aluminum, resistance wires or metal foil wires such as silver) 101-108 and 111-118 each formed by a wiring pattern conductor; terminals 121-128 and 131-138 for acquiring the signal of each gauge lead wire from the crack sensor; and protective films (not shown) for protecting foregoing components from dirt, dust, moisture and the like. Further, an extension direction mark 180 indicated by a shape Δ is formed on the base material 140. The extension direction mark 180 has a function of displaying the vertex direction of the gauge lead wire extending right and left and the extension direction of a crack (the direction of the vertex of the shape Δ).

In the crack sensor 1, by taking the common line 100 as a boundary, a plurality of gauge lead wires 101-108 is arranged in a first area 1A which is located at the left side of the common line 100 and a plurality of gauge lead wires 111-118 is arranged in a second area 1B located at the right side of the common line 100. One end of each of the gauge lead wires 101-108 located in the first area 1A and one end of each of the gauge lead wires 111-118 located in the second area 1B are connected with the common line 100. The gauge lead wires 101-108 located in the first area 1A and the gauge lead wires 111-118 located in the second area 1B are all formed linearly.

The terminals 121-128 are respectively arranged on the other ends of the gauge lead wires 101-108 in the first area 1A and the terminals 131-138 are respectively arranged on the other ends of the gauge lead wires 111-118 in the second area 1B.

If the crack extension direction indicated by the extension direction mark 180 is the upper side, then each of the gauge lead wires 101-108 in the first area 1A and the gauge lead wires 111-118 in the second area 1B is inclined by an angle α by taking the connection point of the gauge lead wire with the common line 100 as its vertex and a corresponding one of the terminals 121-128 and 131-138 as its lower end side.

If the extension direction of the extension direction mark 180 is set to the Y axis and the direction orthogonal to the Y axis to the X axis, then the terminals 121-123 in the first area 1A are arranged on an axial line Xa and the terminals 123-128 are arranged on an axial line Ya. Similarly, the terminals 131-133 in the second area 1B are arranged on an axial line Xb and the terminals 133-138 are arranged on an axial line Yb.

In the present embodiment, in the gauge lead wires 101-108 in the first area 1A, there is an overlapping area between a gauge lead wire at the upstream side of the direction indicated by the extension mark 180 and an adjacent gauge lead wire at the downstream side of the direction indicated by the extension mark 180 in the X-axis direction. For example, there is an overlapping area C between the gauge lead wire 107 and the adjacent gauge lead wire 108 which is located at the downstream side of the gauge lead wire 107. That is, even if the crack reaching the overlapping area C bends at a right angle to extend towards the side of the terminal 128, the gauge lead wire 108, which indeed exists at the downstream side, is broken by the extending crack. It is the same with the gauge lead wires 111-118 in the second area 1B.

An arrow 160 shown in FIG. 1 represents the extension direction of a crack (crackle) generated on the wall surface of a monitored object such as the concrete or mortar of a bridge or tunnel. As a crack does not necessarily extend linearly, the arrow 160 represents the general extension direction of a crack when the crack sensor 1 is adhered on concrete or mortar.

Further, the crack sensor 1 is pasted on the wall surface of the concrete or mortar of a crack monitored object using an adhesive with the vertex (intersection points of the left and the right leads wires shown in FIG. 1) of the extension direction mark 180 substantially overlapped with the crack extension direction indicated by the arrow 160. The adhesive is a substance containing polyester and the like.

The vertexes of the gauge lead wires can be easily overlapped with the extension direction of a crackle according to the extension direction mark, and thus, the extension status of the crackle can be detected efficiently. Not limited to be shaped into a triangle, the extension direction mark may take any shape as long as a direction with, for example, an arrow is specified.

That is, in the three-layer structure of the present crack sensor consisting of a layer of base material, a layer of wiring pattern, gauge lead wires and terminals and a layer of protective films, the wiring pattern, the gauge lead wires and the terminals are formed in the same layer. Thus, it is hard to cut off the gauge lead wires, avoiding the problem that a crack (fissure) cannot be detected.

In the present embodiment, the common line 100 functions as an under-mentioned electronically common circuit line shown in FIG. 3 (a common ground line, in the present example), and a boundary for separating the gauge lead wires 101-108 in the first area 1A from the gauge lead wires 111-118 in the second area 1B (separating areas).

An lead-out line section 100a extending from the common line 100 is led out at the downstream side of the advancing direction of the crack with respect to the gauge lead wire 118 and the gauge lead wire 108 located at the topmost side (the most downstream side) of the extension direction 160 of a crack. At the leading-out end of the lead-out line section 100a, the terminal 139 is arranged to output a signal to the outside of the crack sensor 1.

In the present embodiment, the common line 100 is used as a common ground line, and thus, the terminal 139 is connected with the ground line of an external circuit of a detector (refer to FIG. 3).

In the present embodiment, a plurality of gauge lead wires 101-108 which is arranged in the first area 1A of the left side linearly symmetrical to a plurality of gauge lead wires 111-118 which is arranged in the first area 1B of the right side at substantially equal intervals with respect to the common line 100 serving as the boundary of the first area 1A and the second area 1B. Apparently, a plurality of gauge lead wires 101-108 in the first area 1A and a plurality of gauge lead wires 111-118 in the second area 1B may be staggered from each other in the Y-axis direction but not necessarily symmetrical to each other with respect to the common line 100. Further, a plurality of gauge lead wires 101-108 in the first area 1A and a plurality of gauge lead wires 111-118 in the second area 1B may not be arranged at certain intervals, instead, the intervals between a plurality of gauge lead wires in the center of the Y-axis direction may be dense.

The terminals 121-128 and 131-138 arranged on the front ends of the gauge lead wires connect the gauge lead wires with an external circuits to acquire, from the external circuit, the change of the signal occurring with the state change of the gauge lead wires (a gauge lead wire is broken or not).

Further, the protective films (not shown) are mainly arranged to insulate the base material, and the gauge lead wires, the wiring pattern conductor and the common line conductor which are arranged on the base material from the outside and protect them from dirt, dust, moisture and other external factors.

FIG. 2 is a diagram illustrating a situation in which a gauge lead wire is broken at a tip position of an extending crack (crackle) when the crack sensor 1 is adhered on a cracked concrete wall surface.

In FIG. 2, the tip position of a crackle is indicated by ▲. In FIG. 2, the crack sensor 1 is adhered at, for example, the initial crack position 401. The crack extends towards the first area 1A side and reaches the first gauge lead wire 101 (a crack tip position 402). Herein, the crack extends substantially towards the left side of the horizontal direction (the X-axis direction). However, as the crack tip position 402 exists in the overlapping area of the first gauge lead wire 101 and the second gauge lead wire 102, the crack extending from the crack tip position 402 reaches the second gauge lead wire 102 (a crack tip position 403).

Then, the crack extends upwards and sequentially reaches the third gauge lead wire 103 (a crack tip position 404) and the fourth gauge lead wire 104 (a crack tip position 405).

The crack extends towards a greatly changed direction (a crack tip position 406), that is, towards the second area 1B side, and reaches the fifth gauge lead wire 115 (a crack tip position 407).

The crack extending substantially horizontally reaches the seventh gauge lead wire 117 (a crack tip position 409) finally. The crack tip positions 407 and 408 on the fifth and the sixth gauge lead wires 115 and 116 in the second area 1B exist in the foregoing overlapping area, thus, the sixth and the seventh gauge lead wires 116 and 117 are indeed broken at crack tip positions 408 and 409 even if the crack extends horizontally.

According to the present embodiment, a crack can be detected even if the crack extends from the crack tip position 402 to the crack tip position 403, from the crack tip position 407 to the crack tip position 408 and then to the crack tip position 409 along a direction substantially orthogonal to the common line 100.

Gauge lead wires are broken as the crack extends towards the foregoing series of directions. In this case, Table 1 shows the output (0 or 1) from each of the terminals 121-128 in the first area 1A and the output (0 or 1) from each of the terminals 131-138 in the second area 1B.

via a lead wire connected with the terminal 139. That is, the voltage of the common line 100 is 0(V).

On the other hand, the gauge lead wires 111-118 in the second area 1B are separately connected, via lead wires connected with the terminals 131-138, with pull-up resistors 231-238 of the interface section 311 and connected with a common power source (voltage VDD) to be pulled up the level of the voltage VDD in voltage.

In the present circuit (crack sensor 1), a gauge lead wire, if not broken, is connected with the common line 100, thus, the output from the terminal of the gauge lead wire becomes a ground level (in the present embodiment, this state is indicated by a logic level 0). Moreover, in a case in which a gauge lead wire is broken, the broken gauge lead wire is connected with the common power source of the voltage VDD via a corresponding pull-up resistor, thus, the voltage of the broken gauge lead wire becomes the level of the voltage VDD (in the embodiment, this state is indicated by a logic level 1).

Further, although the gauge lead wires 101-108 and the terminals 121-128 corresponding to them in the first area 1A are not shown in FIG. 3, a circuit (not shown) for the first area is arranged which is identical to the circuit corresponding to the gauge lead wires in the second area 1B, and the terminals 121-128 are connected with the pull-up resistors (not shown) for the first area. Thus, the same signals as the above are output according to the broken state of the gauge lead wires 101-108.

TABLE 1

| | | TERMINAL NUMBER | | | | | | | | | | | | | | | |
|---|---|---|---|---|---|---|---|---|---|---|---|---|---|---|---|---|---|
| | | 128 | 127 | 126 | 125 | 124 | 123 | 122 | 121 | 138 | 137 | 136 | 135 | 134 | 133 | 132 | 131 |
| TIP POSITION OF CRACK | 401 | 0 | 0 | 0 | 0 | 0 | 0 | 0 | 0 | 0 | 0 | 0 | 0 | 0 | 0 | 0 | 0 |
| | 402 | 0 | 0 | 0 | 0 | 0 | 0 | 0 | 1 | 0 | 0 | 0 | 0 | 0 | 0 | 0 | 0 |
| | 403 | 0 | 0 | 0 | 0 | 0 | 0 | 1 | 1 | 0 | 0 | 0 | 0 | 0 | 0 | 0 | 0 |
| | 404 | 0 | 0 | 0 | 0 | 0 | 1 | 1 | 1 | 0 | 0 | 0 | 0 | 0 | 0 | 0 | 0 |
| | 405 | 0 | 0 | 0 | 0 | 1 | 1 | 1 | 1 | 0 | 0 | 0 | 0 | 0 | 0 | 0 | 0 |
| | 406 | 0 | 0 | 0 | 0 | 1 | 1 | 1 | 1 | 0 | 0 | 0 | 0 | 0 | 0 | 0 | 0 |
| | 407 | 0 | 0 | 0 | 0 | 1 | 1 | 1 | 1 | 0 | 0 | 0 | 1 | 1 | 1 | 1 | 1 |
| | 408 | 0 | 0 | 0 | 0 | 1 | 1 | 1 | 1 | 0 | 0 | 1 | 1 | 1 | 1 | 1 | 1 |
| | 409 | 0 | 0 | 0 | 0 | 1 | 1 | 1 | 1 | 0 | 1 | 1 | 1 | 1 | 1 | 1 | 1 |

In FIG. 2 and FIG. 3, as the common line 100 is broken when the crack extends from the crack tip position 406 to the crack tip position 407, one part of the common line 100 becomes opened. Consequentially, logic levels of the terminals 131, 132, 133 and 134 in the second area 1B change from 0 to 1 (it is the same with terminals 121-124 which are already broken due to the crackle and are therefore not affected).

That is, although not broken (or even usable), the gauge lead wires 111-114 connected with the terminals 131-134 in the second area 1B enter a disenabled state. As a crack scarcely extends towards a reverse direction generally, the gauge lead wires are practically effective.

Further, when the crack extends from the crack tip position 406 to the crack tip position 407, the extension direction of the crackle is substantially parallel to the gauge lead wire 105. Although the crack cannot be detected at this time, the crack can be detected when the crack extends further into the second area 1B of the crack sensor 1 and cracks the gauge lead wire 115.

In FIG. 3, the common line 100 of the crack sensor 1 is connected with the ground level of an interface section 311

FIG. 4 is a block diagram illustrating the structure of a crack monitoring device using the crack sensor shown in FIG. 1 and FIG. 2. In FIG. 4, a wireless transmission is exemplified as a data transmission module for transmitting crack detection data.

The crack monitoring device is provided with the crack sensor 1, a data transmission section 310 configured to acquire the data detected by the crack sensor 1 as digital data and transmit the acquired data, a data receiving and processing section 320 configured to receive the data sent from the data transmission section 310, process the received data as crack data and store the processed data in a memory 324, and a monitor 330 configured to display a monitored result processed by the data receiving and processing section 320.

The data transmission section 310 consists of an interface section 311, a power source 315, a control circuit 314, a wireless circuit 313 and an antenna 312.

The interface section 311 acquires the broken state of the gauge lead wire of the crack sensor 1 as digital data. Further, a ground level is supplied to the common line 100 of the crack sensor 1.

The power source 315 is, for example, a battery such as a cell or a power generation apparatus such as a solar cell used for activating the electric circuit of the data transmission section 310.

The control circuit 314 gives an instruction for the acquisition of the information (data) of the crack tip position shown in Table 1 as digital data via the interface section 311 and the transmission of the data from the wireless circuit section 313 to the data receiving/processing section 320.

The wireless circuit section 313 transmits the data of the crack tip position to the data receiving/processing section 320 according to the instruction from the control circuit 314 via the antenna 312.

A CPU 323 of the data receiving/processing section 320 stores the received data in the memory 324 or transmits the received data to a PC (Personal Computer) (not shown) via an interface section 321. Further, the monitor 330 is connected with the interface section 321. The crack sensor 1 is graphically displayed on the monitor 330 to display a cut gauge lead wire.

That is, the crack monitoring device can read the data of a crackle tip position detected by the crack sensor 1, and thus is capable of monitoring the extension of the crackle.

Further, the crack sensor 1 has an ID number which is added in a sending signal from the data transmission section 310. The data receiving and processing section 320 receives a plurality of data signals from the data transmission section 310 and stores crack data in the memory 324 by each ID number.

With the foregoing structure, a crack generated on the wall surface of a bridge or tunnel can be detected, and the extension of the crack can be managed.

Second Embodiment

Figure 5:
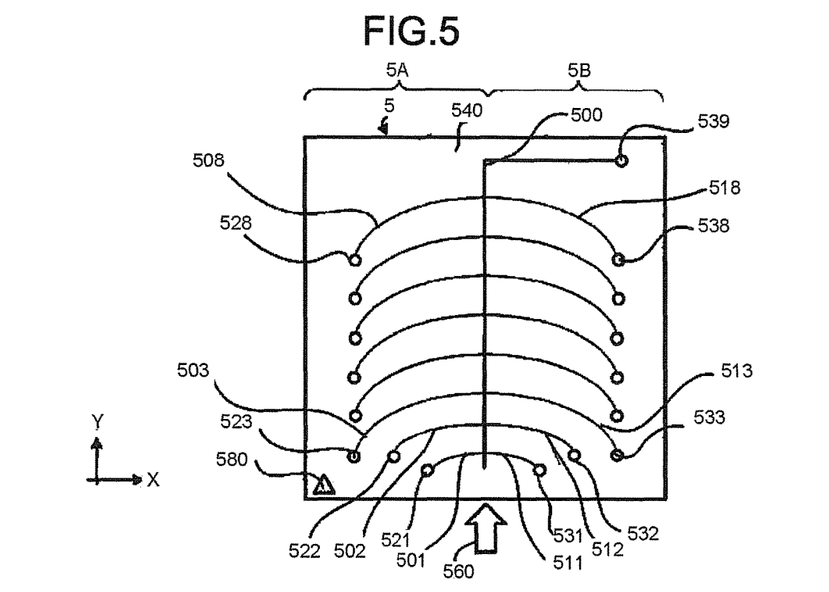
FIG. 5 is a top view of a crack sensor according to a second embodiment.

FIG. 5 illustrates a crack sensor according to the second embodiment.

A crack sensor 5 shown in FIG. 5 is a modification of the crack sensor 1 of the first embodiment. In FIG. 1 and FIG. 5, identical components are denoted by reference signs which are merely different in the first number, that is, the leftmost number of each reference sign shown in FIG. 5 is 5.

In the crack sensor 1 shown in FIG. 1, the gauge lead wires 101-108 located in the first area 1A and the gauge lead wires 111-118 located in the second area 1B are linear and inclined by an angle α. Comparatively, the crack sensor 5 of the second embodiment includes, by taking a common line 500 as a boundary, a plurality of arc-shaped gauge lead wires 501-508 arranged in a first area 5A which is located at the left side of the common line 500 and a plurality of arc-shaped gauge lead wires 511-518 arranged in a second area 5B which is located at the right side of the common line 500. The gauge lead wires are arranged at substantially equal intervals.

That is, centering on the common line 500, a plurality of gauge lead wires 501-508 and a plurality of gauge lead wires 511-518 are symmetrically arranged with a curvature in the first area 5A and the second area 5B.

The gauge lead wires 501-508 and the gauge lead wires 511-518 which are linearly symmetrical to each other with respect to the common line 500 are formed into arcs the vertexes of which are the intersection points of the gauge lead wires 501-508 and 511-518 and the common line 500. Further, the gauge lead wires 501-508 and 511-518 have the same effect as the inclined gauge lead wires according to the first embodiment. Further, in the direction indicated by an extension direction mark 580, there is an overlapping area C in adjacent gauge lead wires 501-508 or 511-518, like in the first embodiment.

An arrow 560 shown in FIG. 5 represents the direction of the extension of a crackle generated in concrete or mortar. As a crackle does not necessarily extend linearly, the arrow 560 represents the general extension direction of the crackle when the crack sensor is attached on concrete or mortar.

The crack sensor 5 is adhered on concrete or mortar using an adhesive with the vertexes of the gauge lead wires 501-508 and 511-518 substantially overlapped with the arrow direction 560 indicating the extension direction of the crackle. The adhesive is a substance containing polyester and the like.

The crack sensor 5 comprises, on a base 540 made from a film-shaped insulating material (polyester resin, polyimide resin, etc.), a common line 500 formed by a wiring pattern conductor (e.g. the alloy of copper and nickel, aluminum and silver), a terminal 539 for connecting the common line with the external of the crack sensor, a plurality of gauge lead wires (e.g. the alloy of copper and nickel, aluminum and silver) 501-508 and 511-518 each consisting of a wiring pattern conductor, terminals 521-528 and 531-538 for acquiring the signal of each gauge lead wire from the crack sensor, and protective films (not shown)

The common line 500 functions as an electrically common circuit wire (a common ground line, in the present example) shown in FIG. 3 and a boundary which separates the gauge lead wires 501-508 from the gauge lead wires 511-518.

In the second embodiment shown in FIG. 5, the crack sensor 5 is linearly arranged in a direction on the wall surface of a monitored object on which a crack occurs. Further, a terminal 539 for outputting a signal to the outside of the crack sensor 5 is connected with the outside of the crack sensor 5. In the present embodiment, the common line 500 is used as a common ground line, and thus, the terminal 539 is connected with the ground line of an external circuit of the detector.

The terminals 521-528 and 531-538 are separately connected with the front ends of the gauge lead wires to connect the gauge lead wires with the outside to output, from the external circuit, the change of the signal occurring with the state change of the gauge lead wire (the gauge lead wire is broken or not).

The protective films (not shown) are mainly arranged to insulate the base material, and the gauge lead wires, the wiring pattern conductor and the common line conductor which are arranged on the base material from the outside and protect them from dirt, dust and other external factors.

The crack sensor 5 of the present embodiment is used after being connected with the interface circuit shown in FIG. 3. The operation principle described in the present embodiment is the same as that described in the second embodiment and is therefore not described here.

The crack sensor 5 of the present embodiment is adhered nearby the monitored concrete or mortar in which a crack is already occurs to detect the extension of the crack. The crack sensor 5 is adhered on the monitored object using an adhesive with the vertexes (∧) of the gauge lead wires overlapped with the extension direction (the head) of the crack. In this case, with the use of the extension direction mark 580, the crack sensor 5 is adhered with the vertex of the triangle Δ being the vertex direction of the gauge lead wires (that is, the extension direction of the crack). The vertexes of the gauge lead wires can be easily overlapped with the extension direction of a crack based on the extension direction mark 580, and thus, the extension status of the crack can be detected more efficiently. Not limited to be shaped into a triangle, the extension direction mark may take any shape as long as a direction with, for example, an arrow is specified.

Third Embodiment

Figure 6:
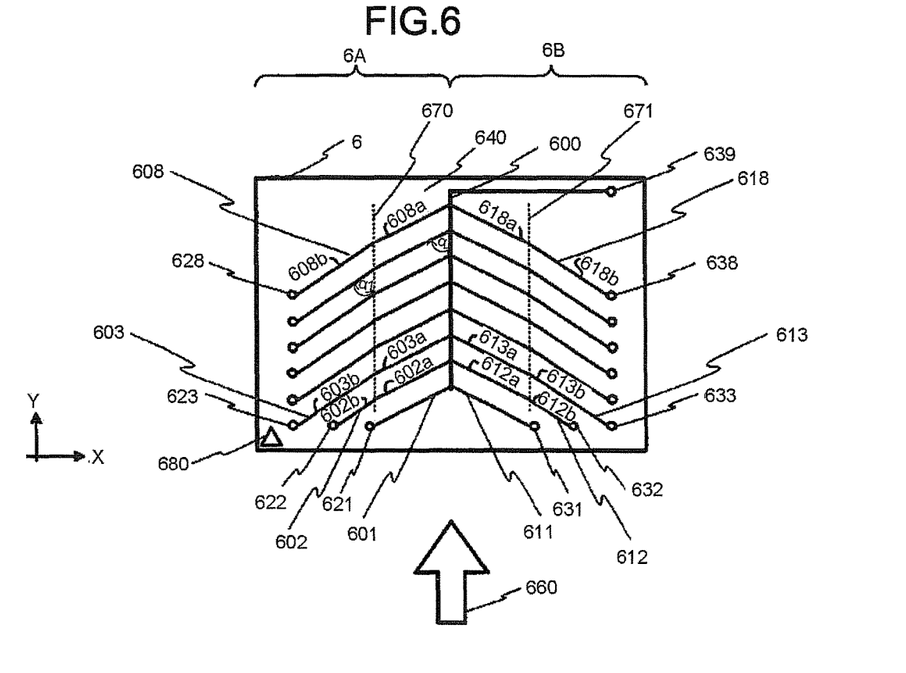
FIG. 6 is a top view of a crack sensor according to a third embodiment.

FIG. 6 illustrates a crack sensor of the third embodiment.

A crack sensor 6 shown in FIG. 6 is a modification of the crack sensor 1 of the first embodiment. In FIG. 1 and FIG. 6, identical components are denoted by reference signs which are merely different in the first number, that is, the leftmost number of each reference sign shown in FIG. 6 is 6.

The crack sensor 6 of the third embodiment is identical to the crack sensor 1 shown in FIG. 1 in basic structure but different from the crack sensor 1 in that each of the gauge lead wires 602-608 in the first area 6A and each of the gauge lead wires 612-618 are both formed by two lines that are inclined by different angles.

The gauge lead wires 602-608 in the first area 6A each have a bending point in the line indicated by the straight line 670. Each of the gauge lead wires 602-608 consists of one of lead wire sections 602a-608a next to the common line 600 and one of curved gauge lead wire sections 602b-608b next to the terminals 622-628, wherein the lead wire sections 602a-608a and the curved gauge lead wire sections 602b-608b take the bending point as a boundary. The lead wire sections 602a-608a are inclined by an angle α, and the curved gauge lead wire sections 602b-608b are inclined by an angle α1 (α1<α).

The gauge lead wires 612-618 in the second area 6B each have a bending point in the line indicated by the straight line 671. Each of the gauge lead wires 612-618 consists of one of lead wire sections 612a-618a next to the common line 600 and one of curved gauge lead wire sections 612b-618b next to the terminals 632-638, wherein the lead wire sections 612a-618a and the curved gauge lead wire sections 612b-618b take the bending point as a boundary. The lead wire sections 612a-618a are inclined by an angle α, and the curved gauge lead wire sections 612b-618b are inclined by an angle α1 (α1<α). The gauge lead wires 601-608 arranged in the first area 6A are horizontally symmetrical linearly to the gauge lead wires 611-618 arranged in the second area 6B with respect to the common line 600.

Further, the gauge lead wires 601-608 and 611-618 are arranged at substantially equal intervals in the first and the second areas 6A and 6B. Thus, each gauge lead wire according to the third embodiment acts in the same way with the gauge lead wire according to the first embodiment and therefore is not described here.

According to the third embodiment, for example, a crack reaching the gauge lead wire section 602a of the second gauge lead wire 602 in the first area 6A extends substantially horizontally towards the terminal 623 side of the third gauge lead wire 603. Then, the crack reaches the curved gauge lead wire section 603b of the third gauge lead wire 603. Thus, the third gauge lead wire 603 can practically detect the extension of the crack even if the crack unexpectedly extends along a substantially horizontal direction which is reverse to the direction indicated by the arrow 660.

Fourth Embodiment

Figure 7:
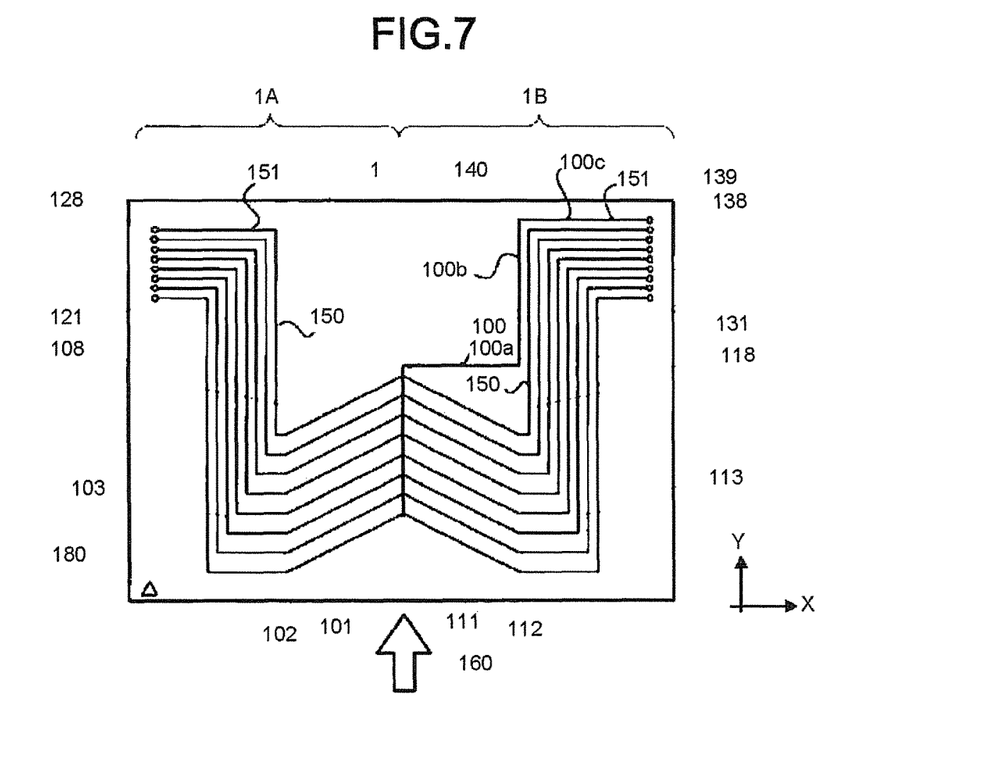
FIG. 7 is a top view of a crack sensor according to a fourth embodiment.

FIG. 7 illustrates a crack sensor of the fourth embodiment.

In the fourth embodiment, the terminals 121-128 and the terminals 131-138 of the gauge lead wires shown in the first embodiment are both arranged collectively. On the base material 140, the terminals 121-128 of the gauge lead wires in the first area 1A and the terminals 131-138 of the gauge lead wires in the second area 1B are arranged at the front end portions at the downstream side of the extension direction of the crack. The terminals 121-128 in the first area 1A are arranged on an axial line parallel to the direction (the Y-axis direction) indicated by the crack extension mark 180. Further, the terminals 121-128 are arranged in the first area 1A at an interval shorter (more densely) than that at which the gauge lead wires 101-108 connected with the common line 100 are arranged. It is the same with the terminals 131-138 in the second area 1B.

The terminal of each of the gauge lead wires 101-108 in the first area 1A opposite to the other terminal of the gauge lead wire connected with the common line 100 is connected with a first connection line 150. The first connection line 150 is arranged facing the front end (the front end in the Y-axis direction) of the direction indicated by the crack extension mark 180. The front end of the first connection line 150 is connected with one end of a second connection line 151 which is arranged horizontally (X-axis direction) facing the terminals 121-128. The other end of each second connection line 151 is connected with one of the terminals 121-128.

Each of the gauge lead wires 111-118 arranged in the second area 1B is also connected with the first connection line 150, and each of the terminals 131-138 arranged in the second area 1B is also connected with the second connection line 151. Apart from the terminals 131-138, a terminal 139 for the common line 100 is also arranged in the second area 1B. Further, a connection line 100b parallel to the first connection 150 and a connection line 100c parallel to the second connection line 151 are arranged on a lead-out line section 100a extending from the common line 100, wherein the front end of the connection line 100c is connected with the terminal 139.

In the present embodiment, the terminals 121-128 and 131-139 are arranged in front of the gauge lead wires in the crack advancing direction 160. Thus, even if the terminals 121-128 or the terminals 131-139 are damaged and the gauge lead wires are broken as the crack extends to the positions of the terminals 121-128 or the terminals 131-139, the crack sensor still functions without being influenced.

Contrarily, for example, if the terminals 121-128 and 131-139 are arranged at the side opposite to that shown in FIG. 7 where the crack advancing mark 180 is arranged. In this case, if the crack extends horizontally, the terminals are damaged, and then an obstacle occurs in the reading of digital data from an interface. This problem can be avoided in the present embodiment.

In the foregoing embodiments, a crack sensor is divided by a boundary of a common line into a first left area in which a plurality of gauge lead wires is arranged and a second right area in which a plurality of gauge lead wires is arranged; however, either of the first and the second areas can function as a crack sensor.

What is claimed is:

1. A crack sensor for detecting the extension of a crack, comprising:
   an insulator base material made from an insulating material;
   a common line formed on the insulator base material along a first direction;
   a lead-out line which extends from an end part of the common line and has a lead-out end;

a plurality of gauge lead wires which are formed on the insulator base material and which extend from the common line to both sides of the insulator base material in a second direction orthogonal to the first direction, wherein the gauge lead wires extend in a direction opposite to an arrangement side of the lead-out end in the first direction as it goes to one or other side of the insulator base material in the second direction, and the gauge lead wires extend away from the common line as it goes to one or other side of the insulator base material in the second direction, and a terminal arranged at an end part of the each gauge lead wire proximate to the one or the other side of the insulator base material to which it was extended.

2. The crack sensor according to claim 1, wherein the gauge lead wires extend from each connecting point arranged on the common line at intervals to both sides of the second direction, and the gauge lead wires comprise;

a plurality of first gauge lead wires which are arranged at one side in the second direction with respect to the common line, the terminals of the respective first gauge lead wires being located at the same distance from the common line in the second direction; and a plurality of second gauge lead wires which are arranged at other side in the second direction with respect to the common line, the terminals of the respective second gauge lead wires being located at the same distance from the common line in the second direction.

3. The crack sensor according to claim 2, wherein the crack sensor has a mark indicating the arrangement side of the lead-out end in the first direction.

4. The crack sensor according to claim 1, wherein the crack sensor has a mark indicating the arrangement side of the lead-out end in the first direction.

5. The crack sensor according to claim 1, wherein the each gauge lead wire is formed in a straight shape or a curve shape.

6. A crack monitoring device for monitoring an extension status of a crack according to information detected by the crack sensor of claim 1, comprising:

a transmission section configured to detect whether or not the first and the second gauge lead wires are cut off and transmits a detection result; and a data receiving and processing section configured to receive the data sent from the transmission section and store the crack data detected by the crack sensor in a memory.

\* \* \* \* \*